US010867699B2

(12) United States Patent
Schneider et al.

(10) Patent No.: US 10,867,699 B2
(45) Date of Patent: Dec. 15, 2020

(54) MEDICATION LIST GENERATOR

(71) Applicant: CERNER INNOVATION, INC., Kansas City, KS (US)

(72) Inventors: Charles Schneider, Trimble, MO (US); Timothy Eugene McCready, Overland Park, KS (US); Christopher Gaul, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 1190 days.

(21) Appl. No.: 14/875,221

(22) Filed: Oct. 5, 2015

(65) Prior Publication Data

US 2017/0098060 A1    Apr. 6, 2017

(51) Int. Cl.
*G16H 20/10* (2018.01)
*G16H 20/00* (2018.01)

(52) U.S. Cl.
CPC .............. *G16H 20/10* (2018.01); *G16H 20/00* (2018.01)

(58) Field of Classification Search
CPC ......... G16H 10/60; G16H 20/10; G16H 20/00
See application file for complete search history.

(56) References Cited

U.S. PATENT DOCUMENTS

| | | | |
|---|---|---|---|
| 8,224,667 B1* | 7/2012 | Miller | G06Q 50/22 705/2 |
| 2006/0200369 A1* | 9/2006 | Batch | A61M 5/16827 705/3 |
| 2009/0157432 A1* | 6/2009 | Palmroos | A61M 5/142 705/3 |
| 2012/0303388 A1* | 11/2012 | Vishnubhatla | G06F 19/328 705/3 |
| 2013/0117044 A1* | 5/2013 | Kalamas | G16H 20/13 705/3 |
| 2014/0157731 A1* | 6/2014 | Perazzo | G01N 21/84 53/473 |
| 2014/0249830 A1* | 9/2014 | Gallopyn | G06F 19/00 705/2 |

FOREIGN PATENT DOCUMENTS

WO    WO-2012145789 A1 *  11/2012  ......... G06F 19/3462

* cited by examiner

*Primary Examiner* — John P Go
(74) *Attorney, Agent, or Firm* — Shook, Hardy & Bacon L.L.P.

(57) ABSTRACT

Methods, systems, and computer-readable media are provided for collecting information regarding the medication an individual is taking before an individual's healthcare visit. A patient medication list is generated using scanned barcode information or information from a photograph taken with the patient's mobile device. The pre-populated medication list is served to a clinician during the individual's healthcare visit without the need for manual entry of each medication the patient is currently taking to speed up the medication reconciliation process.

12 Claims, 4 Drawing Sheets

MEDICATION LIST GENERATOR

BACKGROUND

An electronic medical record (EMR) contains the standard medical and clinical data gathered in one provider's office. An electronic medical record (EMR) is a digital or computerized version of a paper chart that contains all of a patient's medical history from one practice. Information contained in the EMR is typically used by providers for diagnosis and treatment. Electronic health records (EHRs), on the other hand, are designed to contain and share information from all providers involved in a patient's care. EHR data can be created, managed, and consulted by authorized providers and staff from across more than one health care organization. Like, the EMR, an EHR can be used by multiple providers for diagnosis and treatment of the patient.

Some of the standard medical data gathered in the EMR or EHR includes prescribed medications and over the counter medications being taken by a patient. Under current JCHO guidelines, medications for a patient must be reconciled to avoid medication errors. As defined by the JCAHO, medication reconciliation is "the process of comparing a patient's medication orders to all of the medications that the patient has been taking. This reconciliation is done to avoid medication errors such as omissions, duplications, dosing errors, or drug interactions. It should be done at every start or transition of care in which new medications are ordered or existing orders are rewritten. Transitions in care include changes in setting, service, practitioner or level of care.

The medication reconciliation process typically comprises five steps:

1. Develop a list of current medications;
2. Develop a list of medications to be prescribed;
3. Compare the medications on the two lists
4. Make clinical decisions based on the comparison
5. Communicate the new list to appropriate caregivers and to the patient."

The benefits of correctly identifying the medications a patient is taking are significant. Without a correct list of current medications, steps 2-5 of the medication reconciliation process cannot be done correctly or efficiently. Currently, the process of developing a list of current medications when a clinician manually enters, such as typing into a computer interface, each medication and information that is provided to them by the patient or the patient's family. This may be done by verbal communication from the patient to the clinician, by bringing a handwritten list of medications or bringing all of the actual medications and/or medication container with the information regarding the prescription or over the counter medication. Depending on the number of medication and patient's ability to communicate this information, the time to gather and enter the information can take up a significant portion of the clinician visit. Once the list has been input into the computer interface by the clinician, list is then stored in the patient's electronic medical record.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

The claimed invention relates to a system and method supporting computerized healthcare information systems. More specifically, the claimed invention relates to a system and method for computer based healthcare information users to receive information on individual usage in a timely, correct and organized manner a computer based electronic medical record for the patient.

The claimed solution is necessarily rooted in computerized electronic medical record technology in order to overcome a problem specifically arising in the realm of computer healthcare information networks, and the claims address the problem of efficiently and correctly collecting information regarding medication an individual is taking in a computerized healthcare information system before the individual's healthcare visit. If adhering to the routine, conventional function of medication list generation in a healthcare information system, a clinician would manually enter, such as typing in, each medication and medication information individually into the individual's medical record in a computerized healthcare information system during the individual's healthcare visit. This can cause delay and for the incorrect information to be entered.

The claimed invention overcomes the limitations of current computer healthcare information technology and provides other benefits that will become clear to those skilled in the art from the foregoing description.

The claimed system and method of the present application represents a new paradigm of providing medication information in a computerized electronic medical record. Not only does the claimed invention provide clinicians with a current medication list for the patient without manual entry but it also prevents errors in entry of the information and saves time during the patient visit that could be used for patient care. Users of electronic medical records or electronic health records utilizing the claimed invention will notice increased performance of their EMR or EHR, increased retrieval of the medication information from storage, fewer user steps to utilize the EMR and user access to the medication information. Furthermore, anything that reduces the number of "clicks" or entries a computer user has to make in an EMR or EHR results in reducing the memory utilization, CPU cycles, number of operations that need to be performed by the computer, and power consumption. The resulting cost savings and operational efficiencies of a computer electronic medical record magnify the potential benefits of this technology.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for generating a patient medication list for a provider using scanned bar code or information from a photograph.

Figure 1:
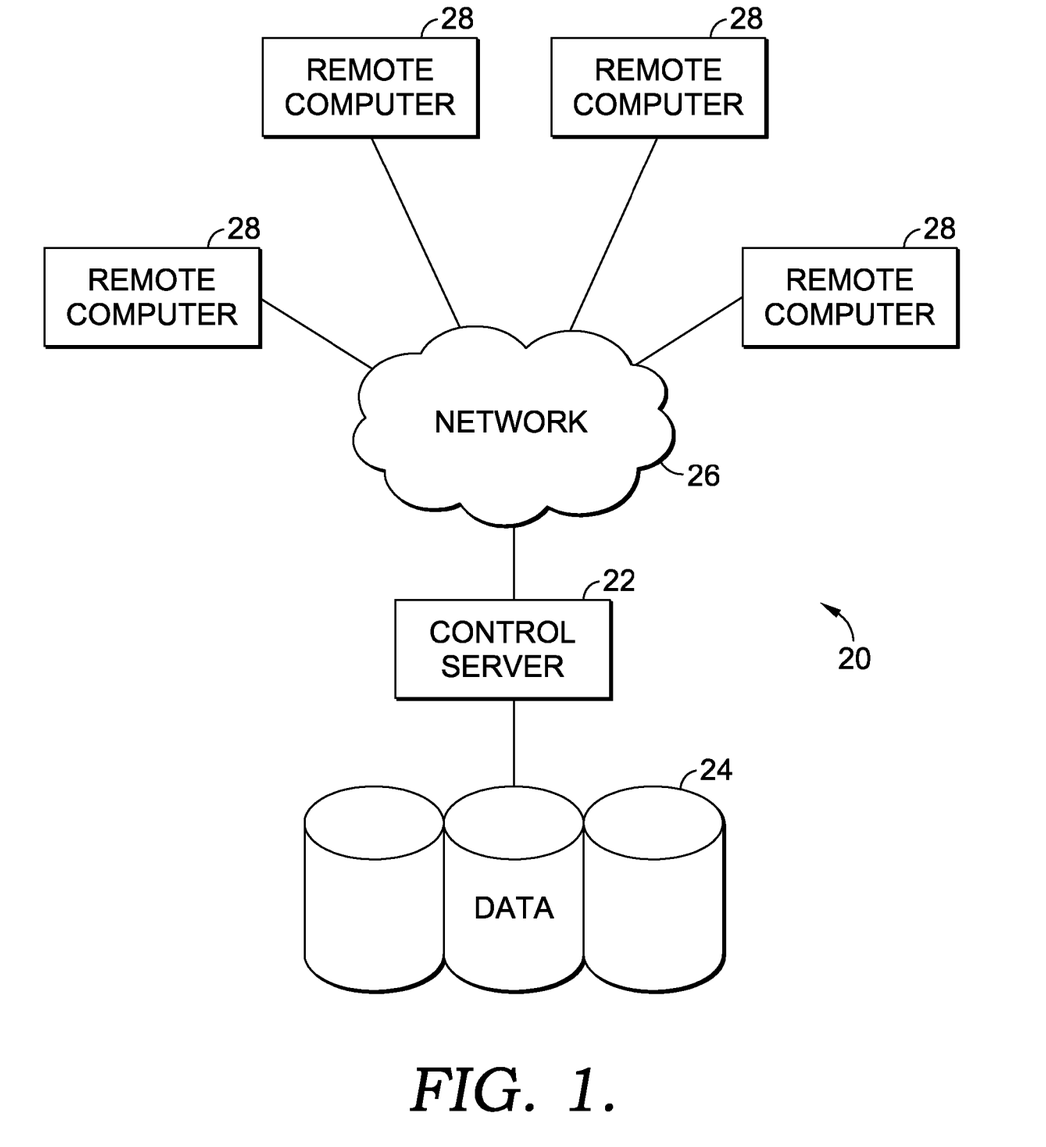
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
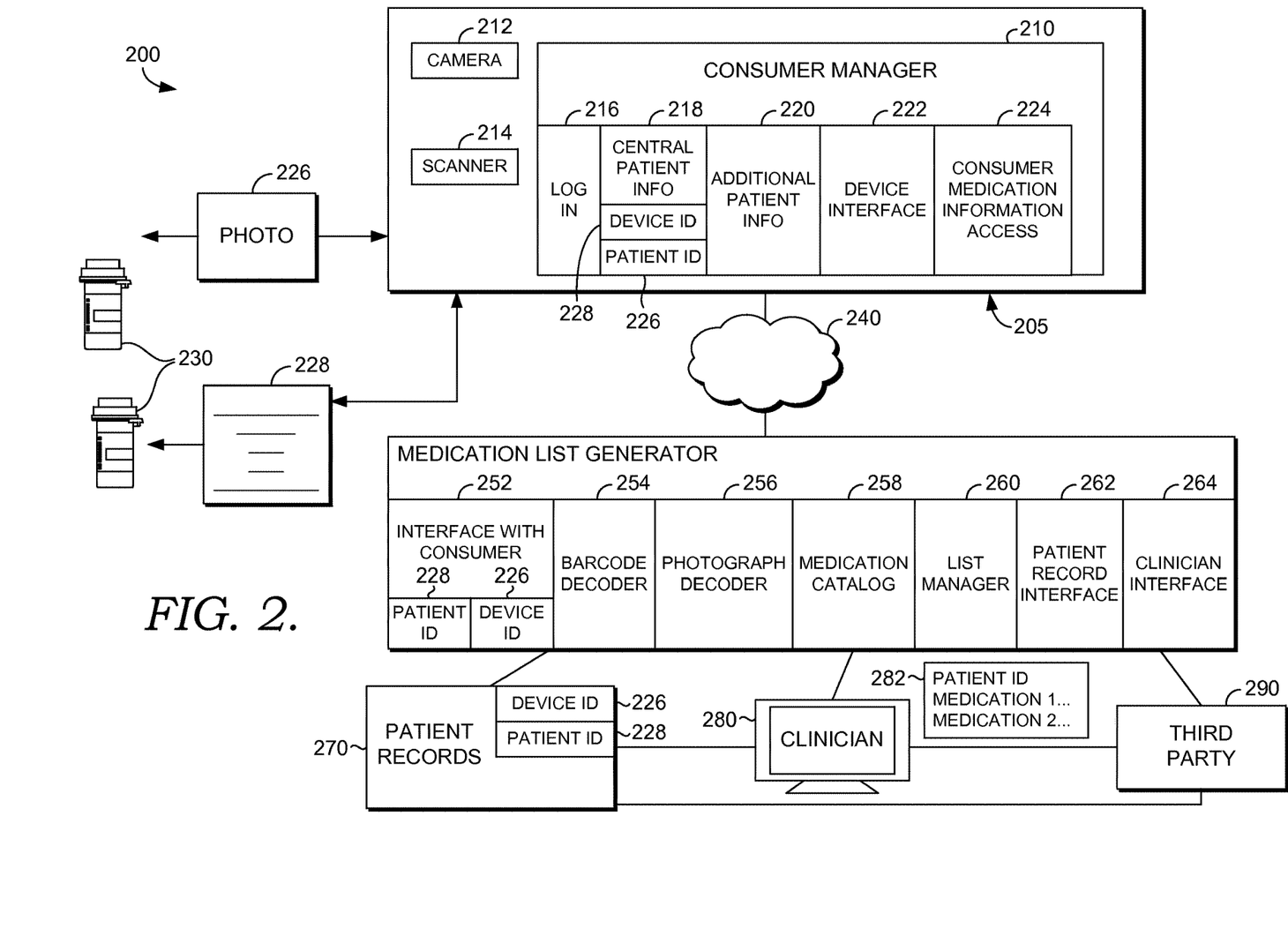
FIG. 2 is a block diagram of an exemplary system for generating a medication list for person suitable to implement embodiments of the present invention.

In an embodiment exhibited by FIG. 2, the processing duties are split among several computing systems. The data store 270 may be implemented through a database system and may be an electronic medical record or electronic health record. The internet 240 serves as a communications link to consumer mobile devices. The tasks performed by the processor utilize a variety of computer technology. In one embodiment, the technology can be divided into three tiers, web server, application server and database server. Each tier is comprised of a number of system layers as described below.

Consumer Manager

Consumer manager 210 is the control center for consumers, such as patients or family members. Consumer manager 210 resides on a personal computing device or mobile device 205 (such a smart phone) of the consumer. Furthermore, consumer manager 210 has an interface 222 with device 205 such that consumer manager 210 can receive information from the camera 212 and scanner 214 residing or connected to device 205.

The consumer manager 210 allows the consumer to communicate with medication list generator 250 and patients' electronic medical records 270 via a network 240. The patient or patient representative may initiate registration of the device 205 via a web interface 216. The signup process will collect basic patient information 218, such as patient identification 228, device identification 226, a password and a unique user id which can be used to login. The patient identification 228 can be transmitted to an EMR such that the correct EMR for the patient is utilized.

When a consumer logs in 216, she is taken directly to a medication consumer manager 210. From the medication consumer manager 210 maintains login screen 216, basic patient information 218 and an API layer between the patient's electronic medical record 240 and the medical consumer manager 210.

The consumer manager 210 is able to maintain additional patient information 220 such as nutrition information (such as calorie and fat gram counting), exercise information (such as counting steps and workouts) as well as other applications such as links to medical devices and monitors. The information maintained in the medication consumer application 210 includes basic consumer information 216 including name, patient number, IP address along with medical contacts, links and interfaces to medical devices, monitors and other medical applications, payment information, pharmacy contact information. The device 205 having the medication consumer application 210 has access to a camera 212 and/or bar code scanner 214 such as those on smart phones, web cameras or personal computers. Consumer manager 210 also includes a consumer medication information component 224 for providing the consumer with a medication list 282 (discussed in detail below) and information regarding the consumer's medications. A consumer can access known medication information via an interface 224 displayed by the consumer manager 210 on the consumer's smart phone or personal computer 205.

Medication List Generator

Medication List Generator 250 is comprised of subcomponents including a consumer interface 252, barcode decoder 254, photograph decoder 256, medication catalog 258, medication list manager 260, electronic medical record interface 262 and clinician interface 264. It will be appreciated that some or all of the modules of medication list generator 250 may reside on consumer device 205 or alternatively some or all of the modules of medication list generator 250 may be accessed via network 240 and reside on device remote to consumer device 205.

Consumer Interface 252

Consumer interface 252 is in communication with consumer manager 210. Consumer manager 210 communicates information such as device id registration 226 and patient identification 228 to consumer interface 252 of medication list generator 250. Consumer interface receives the patient identification 228 and device identification 226 for registration. Interface 252 also receives any scanned barcodes 228 and photographs 226 from consumer manager 210 of device 205. Consumer interface 252 also communicates medication information and medication lists to consumer manager 210 such that the information can be provided to the consumer via consumer medication interface 224 of consumer manager 210.

Barcode Decoder 254

A barcode 228 is scanned by scanner 214 with device 205. The code strings associated with the medication are scanned 228 with the barcode scanner. The scanned barcode information is passed to the consumer manager 210 via device interface 222. The consumer manager 210 communicates the scanned bar code information via consumer interface 252 which is then passed to barcode decoder 254. For example, bar code 310 is scanned from medication bottle 305 of FIG. 3. Medication catalog 258 used to match the scanned bar code information with the medication name, route, dosage and any other identifying information contained in the code strings.

Figure 3:
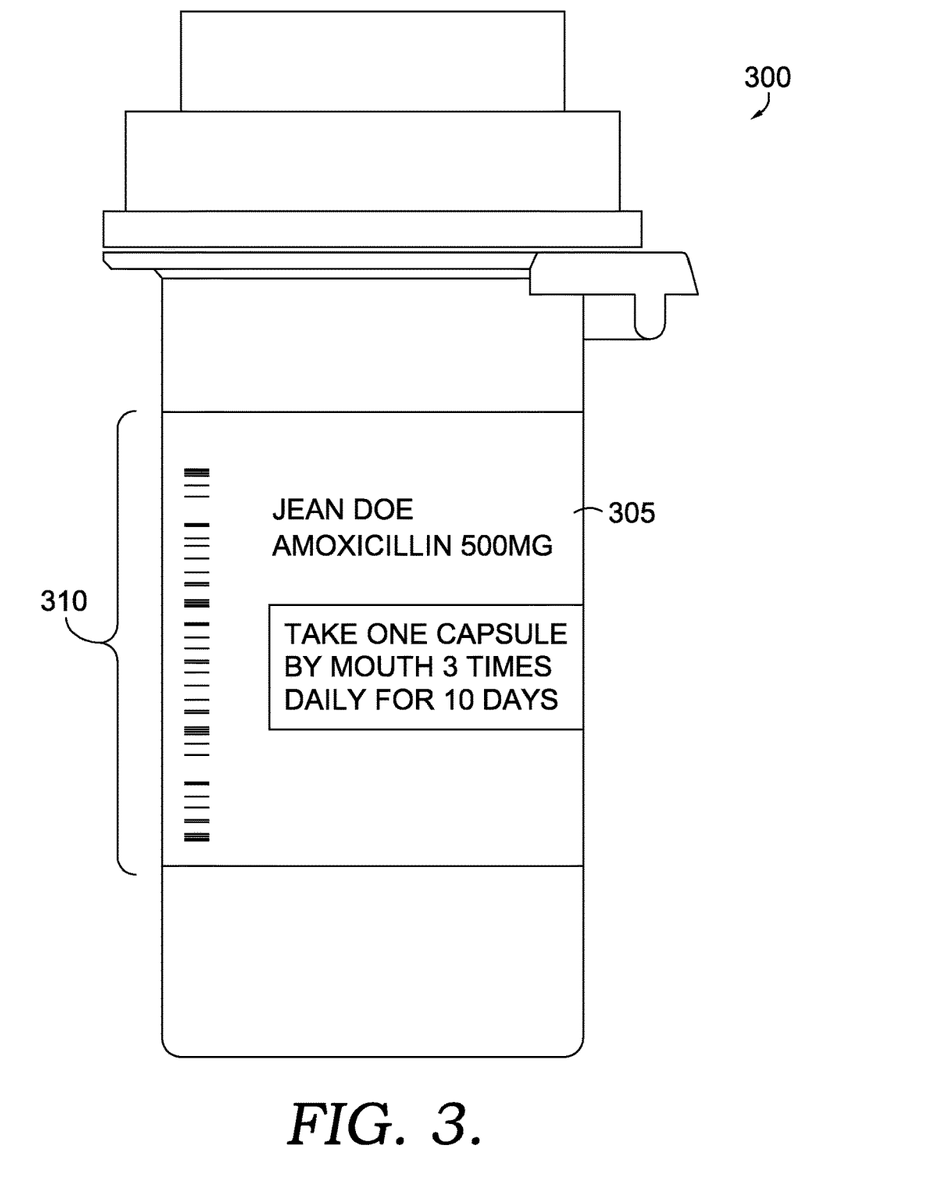
FIG. 3 is a perspective view of a medication bottle with information regarding administration of the medication.

Barcode decoder 254 decodes the medication bar code information 225. For example code received: XYZ XYZ123 XYZ1234 as shown in FIG. 3 corresponds with Amoxicillin 500 mg capsule as shown in FIG. 3. The decoding can be accomplished by matching the bar code information with the correct medication in medication catalog manager 258.

Photograph Decoder 256

A photograph 226 is taken by camera 212 of device 205. For example, a photograph of label 320 is taken of medication bottle 305 of FIG. 3 and/or the actual medication 400 of FIG. 4. The photograph 226 is passed to the consumer manager 210 via device interface 222. The consumer manager 210 communicates the photograph to consumer interface 252 of medication list generator 250 which is then passed to photograph decoder 256.

Figure 4:
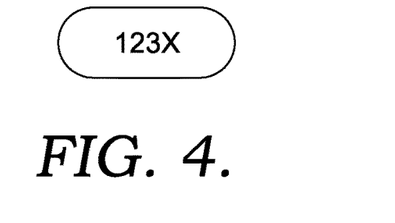
FIG. 4 is a perspective view of an item of medication, such as a pill, in accordance with an embodiment of the present invention.

Photograph decoder 256 utilizes text recognition software to parse as much data from the photograph 226 as possible. For example, photograph decoder would use text recognition to parse the information of the photograph of label 320 received. For example, text recognition would recognize and parse from a photograph:

Patient information—Jean Doe
Route of medication—By Mouth
Frequency of medication—3 times daily
Length of medication—10 days Photograph decoder can also use text and color recognition to parse information from a photograph 400 of the medication itself. For example, photograph decoder 256 can determine that the photograph of pill 400 is a pink capsule having the identification code 123X.

The information parsed from the photographs 225 can then be matched with the correct medication in medication catalog manager 258. For example, the pink pill color and pill code 123X may be contained in medication catalog 258 and listed for amoxicillin 500 mg capsule. As such the parsed photograph information can be matched up with the medication information contained in medication catalog 258. Thus, even in the absence of a barcode with medication information or a prescription label, the consumer can still photograph the actual medication and the parsed and matched information is used to populate the medication list 282 for the consumer discussed in more detail below.

Additionally, additional information can be parsed from a photograph 226 of a medication label or medication itself, including patient information, pharmacy information and prescriber that may not be contained the bar code string or if a bar code string is unavailable. For example code describing the medication, dose and route may be obtained from decoding the barcode but information regarding the frequency, patient name, pharmacy and date prescribed may be parsed from a photograph of the medication label. Alternatively, if there is no bar code 228 available, as much information as possible can be generate by photograph decoder 256 and matching the parsed information using medication catalog 258 of medication list generator 250.

Medication Catalog 258

The medication catalog manager 258 maintains a list drugs and arranges them into catalogs with medication attributes. For example, medication attributes include:

Name of the medication including brand name, generic name, chemical name.

Route that the medication is to be administered (e.g., oral administration, nasal administration, ocular administration)

Frequency refers to how often the medication is to be administered to the patient (e.g., once a day, every 4 hours, as needed).

Length refers to how long the medication is to be administered or prescription should last (e.g., 10 days, 12 hours)

Dosage is the amount of the medication that is to be administered (e.g., 2 pills, 2 drops, 5 cc)

Special instructions provided by the clinician such as "take with food, take at night."

Date Prescribed is the date the medication was prescribed.

Prescribing Clinician is the name, address, clinician identifier and DEA number if needed.

Pharmacy fulfilling medication order is the name, pharmacy identifier that has filled the prescription.

Codes and coding information associated with the medication and the above information.

Information regarding physical characteristic of the medication including color, size, markings and textual codes etched on the medication.

The medication catalog 220 may also maintain updated information for each medication such as drug interactions, adverse events and black box warnings. The catalogs with the medication attributes may include flags to indicate that a medication is subject to a recall, adverse event or has a new black box warning. The medication catalog and medication information is updated on a regular basis by entering new information into medication list generator or alternative automatic updates from drug companies and/or the FDA.

It will be appreciated that the medication catalog 258, medication list manager 260, photograph parser, 256 and barcode decoder 254 may reside on the consumer smart phone or computer 205 or alternatively may be located in another computing environment communicating via a network.

List Manager 260

Medication List Generator 260 leverages information from the consumer manager and/or the patient record to identify the patient using the API layer, communicates with the medication catalog manager to receive the prescription information for the medication.

As medications are scanned or photographed by device 205, decoded by barcoder 254 and photograph decoder 256 and matched to the correct medication and related information using medication catalog 258, a running list of medications and associated information is maintained by list manager 260. For example, when consumer uses a first device to scan barcode 310 of FIG. 3 of medication 1, the information is transmitted, decoded and matched using medication list generator 250. Medication 1 and related information is maintained in list manager 260 along with being tagged with information regarding when the medication was scanned. Below, is an example of medication 1 being added to a medication list using medication list manager 260.

Jean Doe Medication List
Medication 1
Medication and Strength: Amoxicillin 500 mg capsule
Route: By mouth
Frequency: 3 times daily
Length: 10 days starting on April 5
Next in the example, medication 2 is scanned, decoded, matched using medication list generator 250 and is added to a medication list using medication list manager 260.
Jean Doe Medication List
Medication 2
Medication and Strength: Fluticasone Propinoate Nasal Spray 50 mcg
Route: Nasal
Frequency: 1 time daily
Length: As needed The list manager 260 continuously populates the medication list using barcode information or photograph information received from consumer manager 210 using device 205. The medication list 282 for a patient can be viewed by a clinician via an interface 280 displayed by the medication list manager 260 on using clinician interface 264 the clinician's computing device. The medication list 282 can also be presented to the consumer using consumer medication information access 224.

The medication list 282 maintained for the patient in list manager 262 can be annotated by the medication catalog 258 and list manager 260 in a variety of ways before presentation to a clinician and/or the consumer. For example, if certain information for the medication was missing from the information decoded and/or parsed from photograph this would be noted on the medication list and highlighted for the clinician when he/she is reviewing the patient's medication list 282. In another embodiment, if a new black box warning or drug adverse reaction has newly added medication catalog this may be highlighted for the viewing of the clinician and/or consumer.

In embodiments, the list of medications 282 maintained by the list manager 260 and displayed on clinician interface 264 to clinician 280, is a preliminary list that may require additional inputs and verification by the clinician. For example if there is an omission or discrepancy to the preliminary list, this can be input and/or edited by the clinician via clinician interface 264. Once the clinician has made any necessary edits/inputs to the preliminary medication list 282, the clinician verified, finalized and/or approved medication list for the patient for that visit is stored in the patient's electronic medical record 270. Additionally, the verified medication list may be communicated to third party 290, such as an insurance payor, audit agency or application, government entities requiring the information and pharmacies that may need and have permission to access the medication list.

Electronic Medical Record Database

Electronic Medical Record Database 270 is computer store containing healthcare information for individual patients. EMR 270 includes an electronic version of patient records including information for the patient, such as medication and infusion orders, tasks, images, examination reports, testing and lab results, medical history, etc. EMR 270 contains the standard medical and clinical data gathered in a provider's office. An EMR 270 is a digital or computerized version of a paper chart that contains all of a patient's medical history. In the embodiments of the present invention, the patient identifier 228 and patient device identifier 226 are stored in the EMR for the individual patient. Additional, medication names and medication lists 282 may also stored in the patient's EMR.

System Flow

The medication list generator system acts as a clearinghouse for all medications for patient to provide a clinician with a quick and accurate picture of the medications for an individual patient. The system maintains a real-time interface with the a consumer and a clinician including processing medications, recording medications, generating medication lists for access by a clinician and user and generating alerts and action items for both the clinician and consumer. The transaction flow for the clinician is directly related to the structure of the underlying database.

Consumer activates link to consumer manager which in turn activates and registers consumer and consumer's device with the medication list generator and patient's EMR. This activation is typically accomplished by logging into consumer manager by the consumer.

Consumer scans a bar code of a medication using consumer device. The bar code may be on a prescription medication or an over the counter medication. The consumer manager transmits the scanned bar code information to medication list generator at step 505 of FIG. 5 such that the information from the barcode can be translated into a medication for the patient's medication list.

Figure 5:
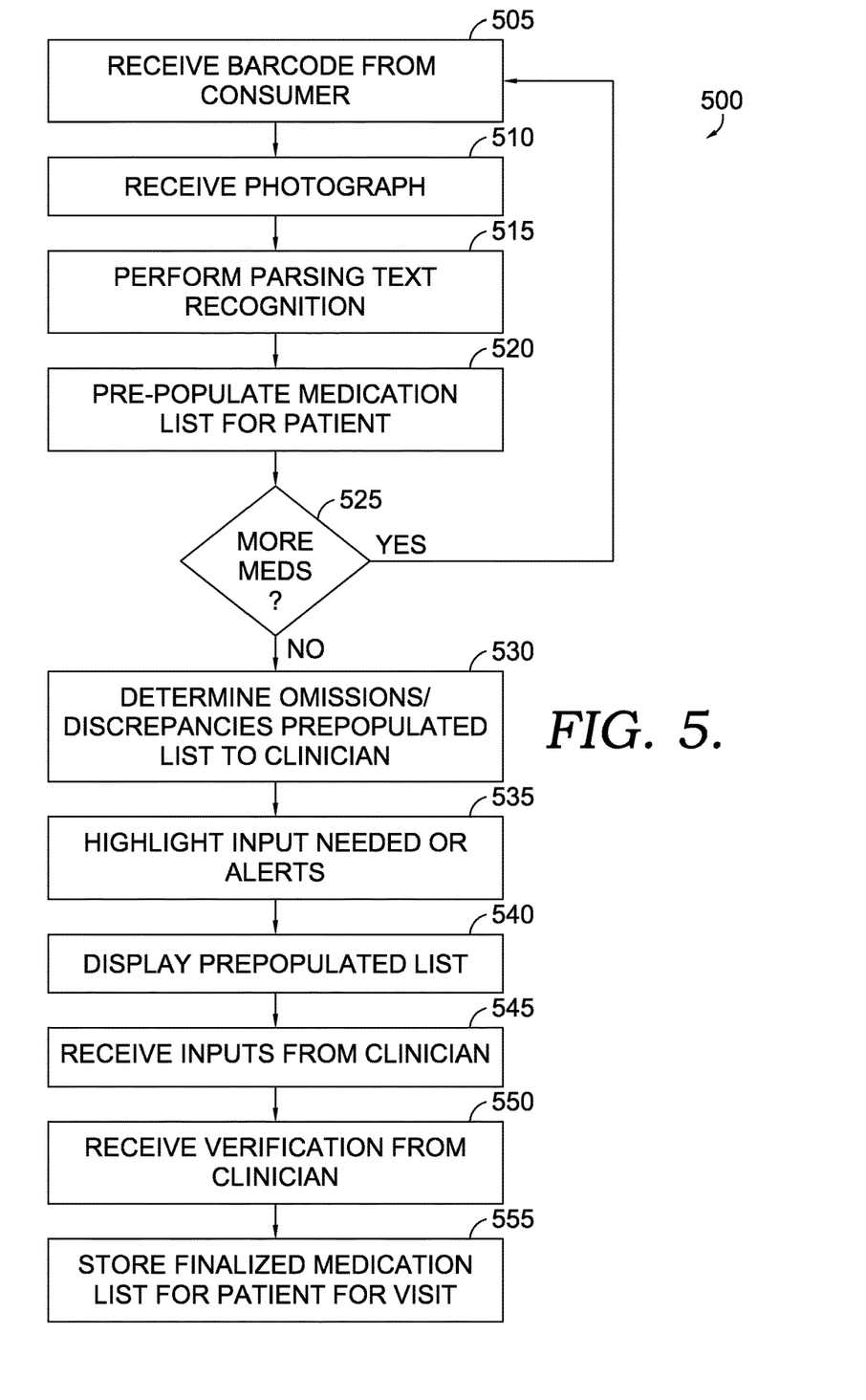
FIG. 5 is a flow diagram of exemplary methods of pre-populating a medication list in accordance with embodiments of the present invention.

Consumer takes a photograph of a medication label using the consumer device. The medication label may be a prescription label or an over the counter label. The consumer manager transmits the photograph to the medication list generator at step 510 such that the information from the photograph can be parsed and translated into medication information for the patient's medication list.

At step 515, the barcode decoder or photograph decoder perform any necessary translation or parsing and text recognition to determine the medication list to populate to the patient's medication list.

At step 520, the medication information, including name, route, dosage, frequency and instructions, are pre-populated to a running medication list for the patient.

Upon the completion of the translation of the first medication scanned and/or photographed at 525 if there are additional medications for the patient being scanned or photographed, steps 505-520 are completed for each of the additional medications.

At step 530, for each medication pre-populated to the medication list, the medication list generator determines any omissions or discrepancies for each medication and makes note of these on the list. For example, if route or duration is missing, these may be highlighted at 535 for the clinician in the clinician interface for the clinician to ask about the missing route or duration for a medication.

The pre-population medication list for an individual patient is presented in to the graphical user interface of the clinician along with any alerts or highlighted omissions or discrepancies. The clinician makes any changes or additions to the pre-populated medication list and verifies or signs the pre-populated list with any changes or additions at 550. At 555, the finalized list is stored in the in the patient's EMR for that patient visit.

As discussed above, a pre-populated medication list can be provided for the patient to a clinician before each visit for the patient as the medications on the patient's list may change from visit to visit. Additionally, the previous medication list can be provided as a template for a clinician, if no new medication has been scanned or photographed by the consumer device since the previous visit. In addition, the verified medication list of current medication can be used to reconcile with newly prescribed medications and utilized to make clinical decisions.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A system useful in a computer healthcare system serving a populated medication list for an individual, the system comprising:
   (a) a computer store containing data, for each of a plurality of medications, defining a plurality of visually perceptible elements, wherein the plurality of visually perceptible elements correspond to a medication and an identification of an individual;
      (i) wherein each of the plurality of medications includes medication information;
      (ii) wherein the identification of an individual includes an identification code that has been linked to an individual's computing device;
   (b) a computer server at the computer healthcare system, which computer server is coupled to the computer store and programmed to:

(i) receive from the individual's computing device a first signal comprising an indication of a first barcode that has been scanned and an indication of a first visually perceptible element;

(ii) automatically decoding by a medication list generator a first source medication from the first barcode that has been scanned;

(iii) automatically identifying by the medication list generator the identification code of the individual from the first signal;

(iv) automatically decoding by a photograph decoder at least one of a route, a frequency, and a duration of the first source medication based on the first visually perceptible element;

(v) in response to identification of the first source medication, automatically populating a medication list comprising the at least one of the route, the frequency, and the duration of the first source medication of the first source medication by the medication list generator, based on the first barcode and the first visually perceptible element; and (vi) receive from the individual's computer device a second signal comprising an indication of a second barcode that has been scanned and an indication of a second visually perceptible element;

(vii) using the medication list generator to automatically decode a second source medication of the second barcode that has been scanned;

(viii) using the medication list generator to automatically identify the identification code of the individual from the second signal, based on the second barcode;

(ix) automatically decoding by the photograph decoder at least one of a route, a frequency, and a duration of the second source medication based on the second visually perceptible element;

(x) in response to identification of the first and second source medication, the medication list generator automatically populating a medication list comprising at least one of the route, the frequency, and the duration with the second source medication by the medication list generator, based on the first and second barcode and the first and second visually perceptible elements;

(xi) detecting the medication list as missing at least one of the route, the frequency, and the duration of the first source medication and/or second source medication by the medication list generator and the medication list, wherein the medication list is based on the first and second barcode and the first and second visually perceptible elements;

(xii) in response to detecting the medication list as missing at least one of the route, the frequency, and the duration, generating an at least one unique visually perceptible element; and (xiii) using the populated medication list and the identification code from the first and second signals and the medication list generator to generate and serve to a browser window that displays:

the medication list comprising at least one of the route, the frequency, and the duration with the first and second source medications of the first and second barcode scans and decoding of the first and second visually perceptible elements with the identification code of the individual; and the at least one unique visually perceptible element.

2. The system of claim 1, wherein the first barcode includes information that can be decoded by the medication list generator for a name, a type and a dose of the first source medication.

3. The system of claim 1, wherein the first barcode includes information that can be decoded by the medication list generator for the frequency and the duration of the first source medication.

4. The system of claim 1, wherein the plurality of visually perceptive elements for the first and second source medication of the barcode scan with the identification code of the individual are served to a clinician for an individual's healthcare visit.

5. The system of claim 1, wherein the plurality of visually perceptive elements for the first and second source medication of the barcode scan with the identification code of the individual are served to the individual's computing device.

6. One or more computer storage media having computer-usable instructions that, when used by one or more computing devices, cause the one or more computing devices to perform a method for serving a populated medication list for an individual to a clinician, the method comprising:

receiving from a patient's mobile device a first signal indicating a first barcode of a medication that has been scanned and an indication of a first visually perceptible element;

automatically decoding by a medication list generator a first source medication from the first barcode that has been scanned;

automatically identifying by the medication list generator an identification code of the individual from the first signal;

automatically decoding by a photograph decoder at least one of a route, a frequency, and a duration of the first source medication based on the first visually perceptible element;

in response to identification of the first source medication, automatically populating using the medication list generator a medication list comprising at least one of the route, the frequency, and the duration of the first source medication with the first source medication based on the first barcode and the first visually perceptible element; and receiving from the patient's mobile device a second signal indicating a second barcode of a second medication that has been scanned and an indication of a second visually perceptible element;

automatically identifying using the medication list generator a second source medication of the second barcode that has been scanned;

using the medication list generator to automatically identify the identification code of the individual from the second signal;

automatically decoding by the photograph decoder at least one of a route, a frequency, and a duration of the second source medication based on the second visually perceptible element;

in response to identification of the first and second source medication, the medication list generator automatically populating based on the first and second barcode a medication list comprising at least one of the route, the frequency, and the duration of the second first source medication with the second source medication based on the first and second barcodes and the first and second visually perceptible elements;

detecting the medication list as missing at least one of the route, the frequency, and the duration of the first source medication and/or second source medication by the medication list generator, based on the first and second barcodes and the first and second visually perceptible elements;

in response to detecting the medication list as missing at least one of the route, the frequency, and the duration, generating an at least one unique visually perceptible element; and using the populated medication list and the identification code from the first and second signals and the medication list generator to generate and serve to a browser window that displays:

the medication list comprising at least one of the route, the frequency, and the duration with the first and second source medications of the first and second visually perceptible elements with the identification code of the individual; and the at least one unique visually perceptible element.

7. The method of claim 6, wherein the first barcode includes information that can be decoded by the medication list generator for a name, type and dose of the first source medication.

8. The method of claim 6, wherein the first barcode includes information that can be decoded by the medication list generator for the frequency and the duration of the first source medication.

9. The method of claim 6, wherein the visually perceptive elements for the first and second source medication of the first and second barcode scan with the identification code of the individual are served to the clinician for an individual's healthcare visit.

10. The method of claim 6, wherein the visually perceptive elements for the first and second source medication of the first and second barcode scan with the identification code of the individual are served to the individual's mobile device.

11. The system of claim 1, wherein detecting the medication list as missing at least one of the route, the frequency, and the duration of the first source medication and/or second source medication by the medication list generator comprises comparing the medication list to a medication catalogue comprising a list of medications and associated information.

12. The system of claim 1, further comprising:

receiving an input corresponding to the unique visually perceptible element;

storing the medication list in a electronic health record (EHR) for the individual.

* * * * *

UNITED STATES PATENT AND TRADEMARK OFFICE
CERTIFICATE OF CORRECTION

PATENT NO. : 10,867,699 B2
APPLICATION NO. : 14/875221
DATED : December 15, 2020
INVENTOR(S) : Charles Schneider et al.

Page 1 of 1

It is certified that error appears in the above-identified patent and that said Letters Patent is hereby corrected as shown below:

In the Specification

Column 02, Line 05: Before "usage" please insert --medication--.

Column 02, Line 06: Before "a" please insert --in--.

In the Claims

Column 12, Line 62: After "second" please remove --first--.

Signed and Sealed this
Eleventh Day of May, 2021

Drew Hirshfeld
*Performing the Functions and Duties of the
Under Secretary of Commerce for Intellectual Property and
Director of the United States Patent and Trademark Office*